United States Patent
Eberstaller et al.

(10) Patent No.: US 10,035,892 B2
(45) Date of Patent: Jul. 31, 2018

(54) FLAME-RETARDANT EXPANDABLE POLYMERS

(71) Applicant: SUNPOR KUNSTSTOFF GESELLSCHAFT M.B.H., St. Poelten (AT)

(72) Inventors: Roman Eberstaller, Obergrafendorf (AT); Gerhard Hintermeier, St. Poelten (AT)

(73) Assignee: SUNPOR KUNSTSTOFF GESELLSCHAFT M.B.H., St. Poelten (AT)

( * ) Notice: Subject to any disclaimer, the term of this patent is extended or adjusted under 35 U.S.C. 154(b) by 0 days.

(21) Appl. No.: 15/243,778

(22) Filed: Aug. 22, 2016

(65) Prior Publication Data

US 2017/0044342 A1 Feb. 16, 2017

Related U.S. Application Data

(63) Continuation-in-part of application No. 14/112,913, filed as application No. PCT/AT2012/000104 on Apr. 17, 2012, now abandoned.

(30) Foreign Application Priority Data

Apr. 18, 2011 (AT) .................. A 549/2011

(51) Int. Cl.
| | |
|---|---|
| *C08J 9/04* | (2006.01) |
| *C08J 9/00* | (2006.01) |
| *C07C 279/02* | (2006.01) |
| *C07F 9/38* | (2006.01) |
| *C07F 9/6571* | (2006.01) |
| *C08J 9/14* | (2006.01) |
| *C08J 9/18* | (2006.01) |
| *C08J 9/224* | (2006.01) |
| *C08J 9/232* | (2006.01) |
| *C09K 21/12* | (2006.01) |

(52) U.S. Cl.
CPC ........... *C08J 9/0038* (2013.01); *C07C 279/02* (2013.01); *C07F 9/3834* (2013.01); *C07F 9/65719* (2013.01); *C07F 9/657181* (2013.01); *C08J 9/0028* (2013.01); *C08J 9/0033* (2013.01); *C08J 9/0066* (2013.01); *C08J 9/141* (2013.01); *C08J 9/18* (2013.01); *C08J 9/224* (2013.01); *C08J 9/232* (2013.01); *C09K 21/12* (2013.01); *C08J 2201/03* (2013.01); *C08J 2201/038* (2013.01); *C08J 2203/14* (2013.01); *C08J 2205/052* (2013.01); *C08J 2205/10* (2013.01); *C08J 2301/10* (2013.01); *C08J 2325/04* (2013.01); *C08J 2325/06* (2013.01); *C08J 2355/02* (2013.01); *C08J 2467/00* (2013.01); *C08J 2481/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,811,470 A | * | 9/1998 | Prindle, Jr. ............... | C08K 3/06 521/85 |
| 2008/0058435 A1 | * | 3/2008 | Allmendinger ........ | C08J 9/0038 521/107 |
| 2012/0264837 A1 | | 10/2012 | Eberstaller et al. | |

FOREIGN PATENT DOCUMENTS

| | | |
|---|---|---|
| AT | 508304 A1 | 12/2010 |
| WO | WO 2011/000019 A1 | 1/2011 |
| WO | WO 2011/035357 A1 | 3/2011 |

OTHER PUBLICATIONS

International Search Report dated Dec. 5, 2012 from International Application No. PCT/AT2012/000104, 3 pages.

* cited by examiner

*Primary Examiner* — Kara B Boyle
(74) *Attorney, Agent, or Firm* — Kilpatrick Townsend & Stockton LLP

(57) ABSTRACT

The present relates to flame-retardant expandable polymers and to polymer foams and to the use thereof. These flame-retardant expandable polymers and polymer foams can be contained in one or several pressurized containers. According to the present, at least one of the following phosphorus compounds is used as a flame retardant: phosphorus compound according to formula (Ia): (Ia) 10-hydroxy-9, 10-dihydro-9-oxa-10-phosphaphenanthrene-10-oxide (DOPO-OH); or the salts thereof according to formula (Ib): (Ib) (DOPO-OR); or the ring-opened hydrolysates thereof according to formula (Ic): (Ic).

17 Claims, No Drawings

FLAME-RETARDANT EXPANDABLE POLYMERS

CROSS-REFERENCED TO RELATED APPLICATIONS

This application is a Continuation-in-Part of U.S. application Ser. No. 14/112,913, filed on Jan. 7, 2014, and entitled "FLAME-RETARDANT EXPANDABLE POLYMERS," which is a National Stage of International Application No. PCT/AT2012/000104 filed on Apr. 17, 2012, and which claims the benefit of Austrian Application No. A 549/2011 filed Apr. 18, 2011, the disclosures of each of which are hereby incorporated by reference herein.

FIELD OF THE DISCLOSURE

The present invention relates to flame-retardant expandable polymerizates containing at least one propellant, in which at least one phosphorus compound is contained as a flame retardant.

The invention further relates to methods of preparing these polymerizates, polymeric foams protected by these flame retardants, methods of preparing the same, as well as the particular use of the above flame retardants in expandable polymerizates and polymeric foams.

PRIOR ART

Equipping polymeric foams with flame retardants is important and/or mandatory in many fields. Regulations on the use of polystyrene particle foams made of expandable polystyrene (EPS) or polystyrene extrusion foam plates (XPS) as heat-insulating material for buildings require flame-retardant equipment in most cases. Polystyrene homo- and copolymers are predominantly rendered flame-resistant using halogen-containing, particularly brominated, organic compounds such as hexabromocyclododecane (HBCD). However, this and a number of other brominated substances have been subject to debate and/or already banned due to the potential environmental and health hazard they pose.

As an alternative, numerous halogen-free flame retardants exist. However, halogen-free flame retardants require to be used in substantially higher amounts for achieving the same flame-retardant effect as the halogen-containing flame retardants.

It is partly for this reason that halogen-free flame retardants, which can be employed in compact thermoplastic polymers, cannot be used in the same manner in polymeric foams as they either interfere with the foaming process or affect the mechanical and thermal properties of the polymeric foam. Moreover, in preparing expandable polystyrene by suspension polymerization, the high amounts of flame retardant may reduce stability of the suspension and thus interfere with and/or affect the preparation procedure.

The effect of the flame retardants used in compact polymers is often unpredictable in polymeric foams, due to the particularities of such foams and due to differing fire tests.

In this respect, prior art application WO 2006/027241 describes a halogen-free flame retardant for polymeric foams, which does not substantially affect the foaming process and allows preparing predominantly closed-cell polymeric foams. This flame retardant is a phosphorus compound that has been known and used since the early 1970s and can be prepared, for example, according to JP-A 2004-035495, JP-A 2002-069313 or JP-A 2001-115047. Particularly preferably, though not exclusively, the phosphorus compound 9,10-dihydro-9-oxa-10-phosphaphenantrene-10-oxide (6H-dibenzo[c,e]-oxaphosphorine-6-oxide, DOP-O, CAS [35948-25-5]) is mentioned:

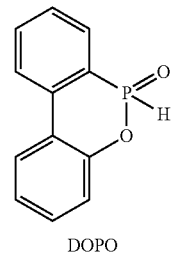

DOPO

This flame retardant is already good to use, however, there is a need for rendering such polymerizates and polymeric foams even more flame resistant while employing a preferably low content of flame retardants and/or without increasing the flame-retardant content. In addition, DOPO has a softening effect in polymerizates, especially in styrene polymerizates, so that, with sufficient flame-inhibiting effect, the requirements regarding mechanical stability employed in most European states for construction products cannot be achieved. This is an essential drawback of DOPO, excluding the use of DOPO in foamed polymers.

AT 508,304 describes that the concentration of DOPO, and thus its softening effect, can be reduced by adding sulfur and/or at least one sulfur-containing compound and/or sulfur compound to the extent that polymeric foams can be prepared, which meet the minimum requirements for foamability and mechanical stability. However, the softening effect could not be abolished entirely, only reduced.

AT 508,507 describes 9,10-dihydro-9-oxa-10-phosphaphenanthrene-10-thione or -10-sulfide (DOPS) as well as a number of derivatives thereof. However, it is an unpleasant side effect especially of sulfur, but also of many sulfur compounds, that odor-intensive compounds can be generated, for example, in processing.

It is thus an aim of the present invention to create a sufficiently fire-resistant, flame-retardant, expandable polymerizate with a low flame-retardant content and good quality, in particular good foamability and good mechanical stability, and non-irritating odor properties.

It is also an aim of the invention to create an advantageous method for preparing such polymerizates.

Another aim of the invention is to create a halogen-free polymeric foam with still appropriate quality, having beneficial fire behavior and good mechanical properties as well as an advantageous method of preparing the same.

It is thus particularly desirable that the polymerizate and/or the polymeric foam meet the rigid requirements regarding fire resistance, e.g. for construction applications such as, for example, the B2 small-burner test according to EN 11925-2.

DISCLOSURE OF THE INVENTION

This aim is reached for the polymerizate of the above-mentioned kind by the characteristic features of Claim 1. According to the invention, it is thereby intended that at least one of the following phosphorus compounds is contained as a flame retardant:

phosphorus compound according to formula (Ia):

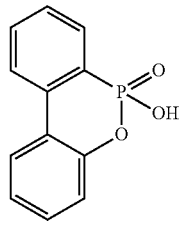

(Ia)

10-hydroxy-9,10-dihydro-9-oxa-10-phosphaphenan-threne-10-oxide (DOPO-OH)

or salts thereof according to formula (Ib):

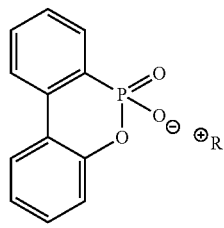

(Ib)

(DOPO-OR)

or ring-opened hydrolyzates thereof according to formula (Ic):

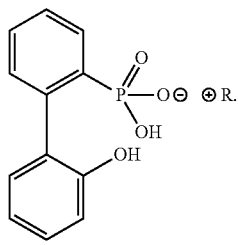

(Ic)

Using these phosphorus compounds, high-quality, sufficiently fire-resistant polymerizates that meet legal standards can be achieved already at low flame-retardant contents. The polymerizates have good foamability, good mechanical stability and no irritating odor properties.

Advantageous advancements of these polymerizates are described by the features of the dependent claims:

For example, it is possible that the residue $R^+$ is an organic or inorganic cation, particularly a salt of a quaternary ammonium compound $NR_4^+$ or a quaternary phosphonium compound $PR_4^+$, as these may also contribute to the flame-retardant effect. The ammonium and phosphonium compounds may have up to four organic residues (i.e. $NR_4^+$ and/or $PR_4^+$) instead of hydrogen atoms.

In this context, it has been found especially beneficial if residue $R^+$ in general formula (Ib) or (Ic) is $NH_4^+$ and the phosphorus compound is 10-hydroxy-9,10-dihydro-9-oxa-10-phosphaphenanthrene-10-oxide ammonium salt:

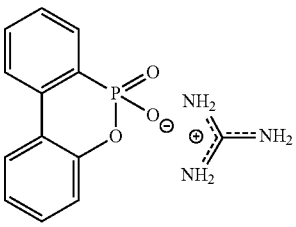

DOPO-ONH₄

It has also been found to be especially advantageous if residue $R^+$ in general formula (Ib) or (Ic) is guanidinium and the phosphorus compound is 10-hydroxy-9,10-dihydro-9-oxa-10-phosphaphenanthrene-10-oxide guanidinium salt:

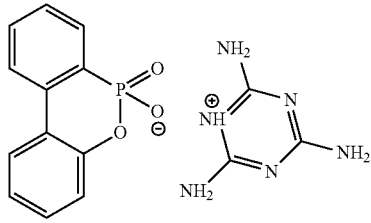

DOPO-OGua

It has also been found to be especially beneficial if residue $R^+$ in general formula (Ib) or (Ic) is melaminium and the phosphorus compound is 10-hydroxy-9,10-dihydro-9-oxa-10-phosphaphenanthrene-10-oxide melam inium salt:

DOPO-OMel

As shown in exemplary embodiments below, these new compounds alone or as a mixture of several of them or as part of a flame-retardant composition, exhibit excellent flame-retardant properties. Using these flame retardants, polymerizates and polymeric foams with improved flame-retardant effect and improved properties can be created. Moreover, comparatively lower amounts—which do not interfere with the foaming process—are sufficient to achieve the same effect. In particular, these compounds do not have troublesome softening properties. It was surprisingly found that such flame-retardant polymerizates and polymeric foams have improved mechanical stability at unexpected levels, compared, for example, to the compound DOPO.

These new compounds can be contained within one or several pressurized containers and can be dispensed from these one or several pressurized containers. In some embodiments, these one or several pressurized containers can comprise, for example, a fire extinguisher, a horizontal pressure vessel, and/or a vertical pressure vessel. In some embodiments, the one or several pressure vessels can comprise a material that is non-reactive with these new compounds. In some embodiments, these new compounds can be applied to one or several items and/or one or several structures from the one or several pressurized container so as to thereby improve increase the flame retardance of the one or several items and/or one or several structures.

Also, no irritating odors are created in processing.

It is advantageously intended that the phosphorus phosphorus compound(s) is/are contained at an amount of 0.5 to 25% by weight, particularly 1 to 15% by weight, based on the total weight of the polymer and/or of the granules thus obtained.

For enhancing the flame-inhibiting effect, it is advantageous to use synergists, which, by themselves, have no or only little flame-inhibiting effect but surprisingly enhance the flame-inhibiting effects in combination with said phosphorus compounds.

In doing so, sulfur and/or sulfur-containing compounds and/or sulfur compounds have been found to be particularly useful as synergists, in particular in amounts of 1 to 25% by weight, in particular 2 to 15% by weight, based on the total weight of the polymer.

As sulfur compounds, for example, sulfides, sulfites, sulfates, sulfanes, sulfoxylates, sulfones, sulfonates, thiosulfates, thionites, thionates, disulfates, sulfoxides, sulfur nitrides, sulfur halogenides and/or organosulfur compounds such as thiols, thioethers, thiophenes, etc., can advantageously be used.

Furthermore, those sulfur compounds have been found to be of advantage which exhibit a weight loss of less than 10% by weight in an analysis using thermogravimetry (TGA) according to EN ISO 11358 below 115° C., such as ammonium thiosulfate, dicaprolactam disulfide, zinc sulfide, polyphenylene sulfide, etc.

It is particularly advantageous, if the sulfur-containing compound and/or sulfur compound has at least one S—S bond, wherein at least one of said sulfur atoms is present in the bivalent form, such as disulfites, dithionites, cystine, amylphenol disulfide, polytert-butylphenol disulfide, etc.

Surprisingly, thiosulfate compounds such as melaminium thiosulfate (MeITS)

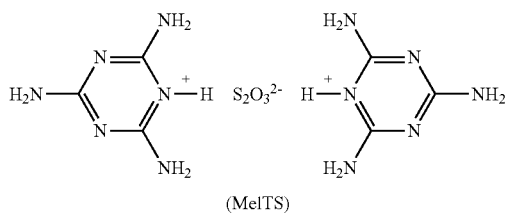

(MeITS)

and the para-tertiobutylphenol disulfide polymer

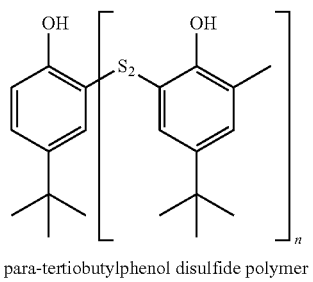

para-tertiobutylphenol disulfide polymer have been found to be particularly effective.

It was also surprising how comparatively low-odor the synergists melaminium thiosulfate and para-tertiobutylphenol disulfide polymer are. By using these synergistic sulfur compounds, the total amount of flame retardants can additionally be reduced, which brings about a plurality of advantages regarding, among others, the production process, costs, mechanical properties of the product, etc. Most importantly, the foaming process and the mechanical properties of the foam are affected only unsubstantially, which allows for a high-quality product.

The inventive expandable polymerizates are preferably expandable styrene polymerizates (EPS) and/or expandable styrene polymer granulates (EPS), consisting particularly of homo- and copolymers of styrene, preferably crystal-clear polystyrene (GPPS), high-impact polystyrene (HIPS), anionically polymerized polystyrene or high-impact polystyrene (A-IPS), styrene-alpha-methylstyrene copolymers, acrylonitrile-butadiene-styrene polymerizates (ABS), styrene-acrylonitrile (SAN), acrylonitrile-styrene-acrylic ester (ASA), methylacrylate-butadiene-styrene (MBS), methyl-meth-acrylate-acrylonitrile-butadiene-styrene (MABS) polymerizates, or mixtures thereof or mixtures with poly (phenylene ether) (PPE). Particularly for polystyrene, the need for high-quality products is particularly high.

Also, this flame-retardant system is suitable for thermoplastic polymerizates such as cellulose acetate butyrate (CAB) as well as for expandable polymerizates consisting of poly(lactic acid) (PLA) or contain poly(lactic acid) (PLA).

For improving their mechanical properties or temperature resistance, the styrene polymers mentioned above may be blended with thermoplastic polymers such as polyamides (PA), polyolefins, e.g. polypropylene (PP) or polyethylene (PE), polyacrylates, e.g. poly(methyl methacrylate) (PMMA), polycarbonate (PC), polyesters, e.g. poly(ethylene terephthalate) (PET) or poly(butylene terephthalate) (PBT), polyethersulfones (PES), polyether ketons or polyether sulfides (PES), or mixtures thereof usually in contents of altogether up to 30% by weight, preferably in the range from 1 to 10% by weight, based on the polymer melt, optionally using tolerance mediators.

Moreover, mixtures in the above amount ranges are possible also, for example, with hydrophobically modified or functionalized polymers or oligomers, rubbers such as polyacrylates or polydienes, e.g. styrene-butadiene block copolymers, biodegradable aliphatic or aliphatic/aromatic copolyesters or thermoplastic polymers such as cellulose acetate butyrate or thermoplastic polyurethane.

Suitable tolerance mediators include, for example, maleic anhydride-modified styrene copolymers, epoxy group-containing polymers or organosilanes.

The effectiveness of phosphorus compounds can be further improved by adding suitable flame-retardant synergists such the thermal radical-forming agents dicumyl peroxide, di-tert-butyl peroxide, or dicumyl.

In addition, other flame retardants such as melamine, melamine cyanurates, metallic oxides, metallic hydroxides, phosphates, phosphinates or synergists such as $Sb_2O_3$ or Zn compounds can also be used.

If complete halogen-freedom of the polymerizate or polymer foam is dispensable, foams with reduced halogen contents can be employed by using phosphorus compounds and adding minor amounts of halogen-containing, particularly brominated, flame retardants such as hexabromocyclododecane (HBCD), preferably in amounts in the range of 0.05 to 1, in particular 0.1 to 0.5% by weight.

Another aspect of the invention relates to the preparation of such polymerizates. According to the invention, the above-mentioned flame-retardant, expandable polymerizates can be prepared by admixing the above flame retardants and optionally sulfur and/or at least one sulfur-containing compound and/or sulfur compounds as synergists in a manner known per se.

According to an advantageous protocol, the flame retardant, e.g. DOPO-OH or DOPO-$ONH_4$, the sulfur compound, e.g. melaminium thiosulfate or para-tertiobutyl-phenol disulfide polymer, and a propellant are mixed, using a dynamic and/or static mixer, with a polymer melt such as a styrene polymer melt and then granulated.

Alternatively, the flame retardant retardant, e.g. DOPO-OH or DOPO-$ONH_4$, and the sulfur compound, e.g. melaminium thiosulfate or para-tertiobutylphenol disulfide polymer, may be mixed with the polymerizate, using a dynamic and/or static mixer, and fused, whereafter the melt is contacted with the propellant and granulated.

Alternatively, the flame retardant retardant, e.g. DOPO-OH or DOPO-$ONH_4$, and the sulfur compound, e.g. melaminium thiosulfate or para-tertiobutylphenol disulfide polymer, may be mixed with a still granulated expandable polymerizate, e.g. polystyrene (EPS), and the mixture is then fused and granulated.

Alternatively, the granulate production is conducted by suspension polymerization of the monomers, particularly of styrene, in an aqueous suspension in the presence of the flame retardant, e.g. DOPO-OH or DOPO-$ONH_4$, and the sulfur compound, e.g. melaminium thiosulfate or para-tertiobutylphenol disulfide polymer, and a propellant.

Another inventive method for preparing the inventive flame-retardant expandable styrene polymerizates (EPS) comprises the following steps:
- co-dosing into an extruder: PS or EPS granulate having a molecular weight of Mw>120,000 g/mol, preferably 150,000 to 250,000 g/mol, particularly preferably 180,000 to 220,000 g/mol, as well as the flame retardant, e.g. DOPO-OH or DOPO-$ONH_4$, and the sulfur compound, e.g. melaminium thiosulfate or para-tertiobutylphenol disulfide polymer, and optionally one or more additional additives,
- melting all components inside the extruder;
- optionally admixing at least one propellant;
- mixing all components at a temperature of >120° C.;
- granulating by pressurized underwater granulation at, for example, 1-20 bar, to an granulate size of <5 mm, preferably 0.2 to 2.5 mm, at a water temperature of 30 to 100° C., in particular of 50 to 80° C.;
- optionally coating the surface with coating agents such as silicates, metal salts of fatty acids, fatty acid esters, fatty acid amides.

The inventive halogen-free, flame-retardant, expandable polymers, e.g. styrene polymers (EPS) and styrene polymer extrusion foams (XPS), can be prepared by admixing a propellant, a phosphorus compound of the general formula (Ia) and/or the hydrolyzed product (Ic) and/or a salt thereof (Ib), as well as elemental sulfur and/or a sulfur-containing compound and/or sulfur compound into the polymer melt and then extruding it into foam plates, foam strands, or expandable granules.

Preferably, the expandable styrene polymer has a molecular weight of >120,000, particularly in the range of 180,000 to 220,000, g/mol. Due to the molecular weight reduction by shearing and/or temperature, the molecular weight of the expandable polystyrene is usually about 10,000 g/mol below the molecular weight of the polystyrene used.

Polymer recyclates of the above thermoplastic polymers, in particular styrene polymers and expandable styrene polymers (EPS), can also be admixed to the styrene polymer melt in amounts which do not essentially degrade their properties, usually in amounts of up to 50% by weight, in particular in amounts of 1 to 20% by weight.

Usually, one or more propellants are added to the polymer melt in homogenous distribution at proportions of altogether 2 to 10% by weight, preferably 3 to 7% by weight, based on the polymer melt. The physical propellants typically employed in expandable polystyrene (EPS) are suitable as propellants, such as aliphatic hydrocarbons having 2 to 7 carbon atoms, alcohols, ketons, ethers or halogenated hydrocarbons. Iso-butane, n-butane, iso-pentane, n-pentane are preferably used. For XPS, $CO_2$ or mixtures with alcohols or ketons are preferably used.

The added propellant amount is chosen in order for the expandable polymers, particularly styrene polymers (EPS), to have an expansion capacity of 7 to 200 g/l, preferably 10 to 50 g/l.

The inventive expandable styrene polymer granules (EPS) usually have a bulk density of up to 700 g/l, preferably in the range of 590 to 660 g/l.

Furthermore, additives, germ-forming agents, fillers, softening agents, soluble and unsoluble inorganic and/or organic dyes and pigments, e.g. IR absorbants such as soot, graphite, petcoke, anthrazite or aluminum powder, may be added together or spatially separated, e.g. by mixers and side extruders. Usually, the dyes and pigments are added in amounts in the range from 0.01 to 30, preferably in the range from 1 to 10, % by weight. For homogenous and microdispersed distribution of pigments in the styrene polymer, it can be useful in particular with polar pigments to use a dispersion aid such as organosilane, epoxy-group-containing polymers or chimeric maleic anhydride styrene polymers. Preferred softening agents are mineral oils or phthalates, which may be used in amounts of 0.05 to 10% by weight, based on the styrene polymerizate.

Another aspect of the invention is a polymeric foam, particularly a styrene polymer particle foam or an extruded polystyrene rigid foam (XPS), containing at least one phosphorus compound of the general formula (Ia) and/or ring-opened hydrolyzates or salts thereof as a flame retardant.

For improving the effect, optionally elemental sulfur and/or at least one sulfur-containing compound or sulfur compound can be contained as a flame-retardant synergist.

A particularly preferable polymeric foam is obtainable from the inventive flame-retardant expandable polymerizates, in particular from expandable styrene polymerizates (EPS), in particular by foaming and caking the polymerizates beads or by extruding the granules.

Preferably, the halogen-free flame-retardant polymeric foams have a density in the range from 8 to 200 g/l, particularly preferably in the range from 10 to 50 g/l, and preferably more than 80%, particularly preferably in 95 to 100%, are closed-cell and/or have a predominantly closed-cell structure with more than 0.5 cells per $mm^3$.

According to the invention, at least one of the phosphorus compounds of the general formulae (Ia) and (Ib) and the ring-opened hydrolyzates thereof according to (Ic) is used as a flame retardant, optionally in combination with sulfur and/or a sulfur-containing compound and/or sulfur compound as a flame-retardant synergist, in expandable polymerizates, in particular in expandable styrene polymerizates (EPS) and/or expandable styrene polymer particle foams obtainable by foaming from expandable polymerizates, or in extruded polystyrene rigid foams (XPS).

For producing flame-retardant extruded polystyrene rigid foam (XPS), the phosphorus compounds, the sulfur compounds, and a propellant are mixed with a styrene polymer melt using a dynamic and/or static mixer and then foamed, or the phosphorus compounds and the sulfur compounds are admixed to still granulated polystyrene polymerizates using a dynamic and/or static mixer and fused, and the melt is then contacted with propellant and foamed.

Preparation of the Phosphorus Compounds and of the Synergists:

1. Preparation of 9,10-dihydro-10-hydroxy-9-oxa-10-phosphaphenanthrene-10-one or -10-oxide (DOPO-OH)

a) Preparation of DOPO-OH in an Aqueous Environment:

In a multi-neck flask equipped with mixer, reflux condenser and thermometer, 302.6 g of powdery 9,10-dihydro-9-oxa-10-phosphaphenanthrene-10-oxide (DOPO) were suspended in 327.6 g of water, heated to 90° C. and treated with 190.5 g of 30% hydrogen peroxide over 6 hrs at a temperature of 90-99° C. The suspension was then cooled to room temperature, the precipitate was filtered off and washed with water. Drying of the filter cake was done at 150° C. Crude yield was 312.2 g [96.1% of theory]. After recrystallization from acetic acid, the following data was obtained:

Mp: 203° C. (lit.: 203-204° C.; J. Cadogan, supra)
Elemental analysis $C_{12}H_9O_3P$ (M: 232.17 g/mol):
C calc.: 62.08%; H: 3.91%; P: 13.34%.
C found: 61.5%; H: 4.2%; P: 13.2%.

b) Preparation of DOPO-OH in an Alcoholic-Aqueous Environment:

In a multi-neck flask equipped with mixer, reflux condenser and thermometer, 302.6 g of DOPO were dissolved at 70° C. in 150.0 g of toluene and treated with 317.5 g of 30% hydrogen peroxide at temperatures continuously increasing to 80° C. The suspension thus obtained was cooled down to room temperature, the precipitate was filtered off and washed with methanol. Drying of the filter cake was done at 150° C. Crude yield was 277.1 g [85.3% of theory]. After recrystallization from acetic acid, the following data was obtained:

Mp: 203° C. (lit.: 203-204° C.); phosphorus content: found: 13.3%, calc. 13.34%.

c) Preparation of DOPO-OH in an Aromatic-Aqueous Environment:

In a multi-neck flask equipped with mixer, reflux condenser and thermometer, 302.6 g of DOPO were dissolved at 70° C. in 150.0 g of toluene and treated with 204.1 g of 30% hydrogen peroxide at temperatures continuously increasing to 85° C. 183.7 g of toluene/water mix were then distilled off. The residue was cooled down to room temperature and filtered. Drying of the filter cake was done at 150° C. Crude yield was 314.9 g [96.9% of theory]. After recrystallization from acetic acid the following data was obtained:

Mp: 202-203° C. (lit.: 203-204° C.); phosphorus content: found: 13.2%, calc. 13.34%.

2. Preparation of 9,10-dihydro-10-hydroxy-9-oxa-10-phosphaphenanthrene-10-one or -10-oxide ammonium salts (DOPO-ONH$_4$)

a) Liquid Method:

In a multi-neck flask equipped with mixer, reflux condenser and thermometer, 232.1 g of 9,10-dihydro-10-hydroxy-9-oxa-10-phosphaphenanthrene-10-oxide (DOPO-OH) were suspended in 216.0 g of water and treated with 71.5 g of 25% ammonia at 25° C. The suspension was then heated to 98° C. and afterwards cooled to room temperature. The entire flask contents were emptied onto a drying tray and dried at 120° C.

The yield was 248.4 g [99.7% of theory] of a white, crystalline solid.

Mp: 234-240° C. (dec.)
Elemental analysis $C_{12}H_{12}NO_3P$ (M: 249.20 g/mol):
C calc.: 57.83%; H: 4.85%; N: 5.62%; P: 12.43%.
C found: 57.5%; H: 5.1%; N: 5.5%; P: 12.4% b) Solid Method:

232.0 g of dry ground DOPO-OH with a grain fineness of <45 µm was provided in a closed mill chamber and slowly treated with 78.3 g of ammonia at 25% in water with the shearer in operation. At the end of the ammonia addition, the grist was heated to 77° C. without losing its powdery state. After a 5 minute post-mixing time, the shearer was turned off, and the grist was allowed to rest for 1 h. Subsequently, the grist was re-ground for another 5 minutes and then emptied onto a drying tray, dispersed, and dried at 140° C. The yield was 242 g [97.2% of theory] of a white, crystalline solid, the data of which essentially match those from Example 1.

3. Preparation of 9,10-dihydro-10-hydroxy-9-oxa-10-phosphaphenanthrene-10-one or -10-oxide melaminium salts (DOPO-OMel)

In a multi-neck flask equipped with mixer, reflux condenser and thermometer, 92.8 g of DOPO-OH were suspended in 400 g of water and treated with 50.4 g of melamine at 25° C. The suspension was then heated to 90° C. and maintained at this temperature for 4 hrs. It was afterwards cooled to room temperature. The precipitate was filtered off and washed with water. Drying was done at 160° C., and the yield was 141.4 g [98.7% of theory] of a white, crystalline solid.

Mp: 246-250° C. (dec.)
Elemental analysis $C_{15}H_{15}N_6O_3P$ (M: 358.29 g/mol):
C calc.: 50.28%; H: 4.22%; N: 23.46%; P: 8.64%.
C found: 49.8%; H: 4.5%; N: 23.3%; P: 8.5%

4. Preparation of 9,10-dihydro-10-hydroxy-9-oxa-10-phosphaphenanthrene-10-one or -10-oxide melaminium salts (DOPO-OGua)

In a multi-neck flask equipped with mixer, reflux condenser and thermometer, a mixture of 100.0 g water, 100 g ethanol and 36.0 g guanidium carbonate was prepared and heated to 75° C. Then, 92.8 g of DOPO-OH were titrated over 5.5 hrs. Once no more $CO_2$ development was observed, the reaction mass was condensed by distillation. The remaining crude crystal mash (135.6 g) was applied to a drying tray and dried at 110° C. The yield was 100.5 g [86.0% of theory] of a white, crystalline solid.

Mp: 278-280° C. (dec.)
Elemental analysis $C_{13}H_{14}N_3O_3P$ (M: 291.24 g/mol):
C calc.: 53.61%; H: 4.84%; N: 14.42%; P: 10.63%.
C found: 53.3%; H: 5.1%; N: 14.3%; P: 10.5%

5. Preparation of Melaminium Thiosulfate (MeITS)

a) In a multi-neck flask equipped with mixer, reflux condenser and thermometer, 1218.7 g of distilled water were mixed with 147.8 g of conc. saline (37%) and 189.1 g of melamine. The suspension was heated to reflux. Once a clear solution was obtained, the flask contents were cooled down to 96° C. and treated with 348.6 g of a 34% sodium thiosulfate solution. This brought about a precipitation reaction. The precipitate was cooled down to room temperature with stirring, filtered off and washed intensively with distilled water. Drying of the filter cake was done at 110° C. The yield was 100.5 g [86.0% of theory] of a white, crystalline solid.

Mp: 178-180° C. (dec.)

Elemental analysis $C_6H_{14}N_{12}O_3S_2$ (M: 366.38 g/mol):

C calc.: 19.67%; H: 3.85%; N: 45.88%; O: 13.10%; S: 17.50%.

C found: 19.8%; H: 4.0%; N: 45.6%; O: 13.5%; S: 17.2% b) In a multi-neck flask equipped with mixer, reflux condenser and thermometer, 1200.0 g of distilled water were treated with 252.2 g of melamine and 158.1 g of sodium thiosulfate. The suspension was heated to 95° C. Then 197.1 g of conc. saline (37%) was added dropwise at a dosing rate of 0.9 g/min. Thereafter, the reaction mass was cooled down to room temperature with stirring, the precipitate was filtered off and washed intensively with distilled water. The filter cake was taken up in 1100 g of distilled water again, stirred vigorously and filtered off. Drying of the filter cake was done at 110° C. The yield was 356.8 g [97.4% of theory] of a white, crystalline solid, the data of which essentially match those from Example 1.

c) In a multi-neck flask equipped with mixer, reflux condenser and thermometer, 1130 g of distilled water were mixed with 252.2 g of melamine and 158.1 g of sodium thiosulfate and heated to 90° C. Over 1.5 hrs, 174.2 g of 37.5% phosphoric acid were added dropwise at 90-93° C. Thereafter, the precipitate was cooled down to room temperature with stirring and filtered off via a blue-band filter. The filter cake was washed with water and then dried at 110° C. The yield was 328.5 g [89% of theory] of a white, crystalline solid, the data of which essentially match those from Example 1.

Elemental sulfur, Vultac TB7®, a p-t-butylphenol-disulfide polymer (Arkema), melaminium thiosulfate (bis[(2,4,6-tri-amino-1,3,5-triazinium)thiosulfate, MeITS) (produced by Krems Chemie Chemical Services AG) and ammonium thiosulfate (($NH_4)_2S_2O_3$; ATS, Sigma Aldrich) were used as synergists in the comparative examples.

These examples enable the skilled artisan to prepare and/or obtain the desired flame retardants as such, any required starting products as well as the synergists.

Preparation of the Expandable Polymerizates and of the Polymeric Foams:

The preparation of flame-retardant expandable polymerizates, e.g. of EPS, in the form of granules and/or beads per se is known to skilled artisans. Preparing the polymerizates according to the invention using the above flame retardants and optionally sulfur compounds is done in an essentially analogous way. Thus, for example, the exemplary embodiments of WO 2006/027241, AT 508,304 or AT 508,507 can be used. The same is true for the polymeric foams as well as for XPS.

EXAMPLES

The invention will be described in detail and reproducibly below, referring to specific but not limiting exemplary embodiments. In addition, these examples will be used to demonstrate effectiveness.

The present invention is presently described in detail referring to 19 specific exemplary embodiments 1 through 4, 7 through 12, 15 through 19, 21 and 22 as well as 24 and 25. Examples 5, 6, 13 and 14 are comparative examples, Examples 20 and 23 are reference examples concerning the flame retardant HBCD, which is currently used exclusively in the production of flame-retardant styrene polymer foams (EPS and XPS).

Example 1 (Exemplary Embodiment—DOPO-OH 15%)

To a styrene polymer (SUNPOR EPS-STD: 6% by weight of pentane; chain length MW=200,000 g/mol, multiplicity MW/Mn=2.5), 15% by weight of 10-hydroxy-9,10-dihydro-9-oxa-10-phosphaphenanthrene-10-oxide (DOPO-OH), based on the obtained EPS granules, was admixed in the inlet of a twin-screw extruder and fused at 190° C. within the extruder. The polymer melt thus obtained was passed through a nozzle plate at a throughput of 20 kg/h and granulated into compact EPS granules using a pressurized underwater granulator.

Example 2 (Exemplary Embodiment—DOPO-$ONH_4$ 15%)

Example 1 was repeated with the difference that 15% by weight of 10-hydroxy-9,10-dihydro-9-oxa-10-phosphaphenanthrene-10-oxide ammonium salt (DOPO-$ONH_4$), based on the obtained EPS granules, were dosed.

Example 3 (Exemplary Embodiment—DOPO-OGua 15%)

Example 1 was repeated with the difference that 15% by weight of 10-hydroxy-9,10-dihydro-9-oxa-10-phosphaphenanthrene-10-one or -10-oxide guanidinium salt (DOPO-OGua), based on the obtained EPS granules, were dosed.

Example 4 (Exemplary Embodiment—DOPO-OMel 15%)

Example 1 was repeated with the difference that 15% by weight of 10-hydroxy-9,10-dihydro-9-oxa-10-phosphaphenanthrene-10-one or -10-oxide melaminium salt (DOPO-OMel), based on the obtained EPS granules, were dosed.

Example 5 (Comparative Example—MeITS 15%)

Example 1 was repeated with the difference that 15% by weight of melaminium thiosulfate (MeITS), based on the obtained EPS granules, were dosed (but no phosphorus compound).

Example 6 (Comparative Example—Vultac TB7 15%)

Example 1 was repeated with the difference that 15% by weight of para-tertiobutyl-phenol-disulfide polymer (Vultac TB7 by Arkema company), based on the obtained EPS granules, were dosed (but no phosphorus compound).

Example 7 (Exemplary Embodiment—DOPO-$ONH_4$ 5.0%+MeITS 10.0%)

Example 1 was repeated with the difference that 5% by weight of 10-hydroxy-9,10-dihydro-9-oxa-10-phosphaphenanthrene-10-oxide ammonium salt (DOPO-ONH$_4$) and 10% by weight of melaminium thiosulfate (MeITS), based on the obtained EPS granules, were added.

Example 8 (Exemplary Embodiment—DOPO-OGua 5.0%+MeITS 10.0%)

Example 1 was repeated with the difference that 5% by weight of 10-hydroxy-9,10-dihydro-9-oxa-10-phosphaphenanthrene-10-one or -10-oxide guanidinum salt (DOPO-OGua) and 10% by weight of melaminium thiosulfate (MeITS), based on the obtained EPS granules, were added.

Example 9 (Exemplary Embodiment—DOPO-OMel 5.0%+MeITS 10.0%)

Example 1 was repeated with the difference that 5% by weight of 10-hydroxy-9,10-dihydro-9-oxa-10-phosphaphenanthrene-10-one or -10-oxide melaminium salt (DOPO-OMel) and 10% by weight of melaminium thiosulfate (MeITS), based on the obtained EPS granules, were added.

Example 10 (Exemplary Embodiment—DOPO-ONH$_4$ 5.0%+Vultac TB7 10.0%)

Example 1 was repeated with the difference that 5% by weight of 10-hydroxy-9,10-dihydro-9-oxa-10-phosphaphenanthrene-10-oxide ammonium salt (DOPO-ONH$_4$) and 10% by weight of para-tertiobutylphenol-disulfide polymer (Vultac TB7), based on the obtained EPS granules, were added.

Example 11 (Exemplary Embodiment—DOPO-OH 5.0%+Vultac TB7 10.0%)

Example 1 was repeated with the difference that 5% by weight of 10-hydroxy-9,10-dihydro-9-oxa-10-phosphaphenanthrene-10-oxide (DOPO-OH) and 10% by weight of para-tertiobutylphenol-disulfide polymer (Vultac TB7), based on the obtained EPS granules, were added.

Example 12 (Exemplary Embodiment—DOPO-ONH$_4$ 5.0%+ATS 10.0%)

Example 1 was repeated with the difference that 5% by weight of 10-hydroxy-9,10-dihydro-9-oxa-10-phosphaphenanthrene-10-oxide ammonium salt (DOPO-ONH$_4$) and 10% by weight of ammonium thiosulfate (ATS—Sigma Aldrich), based on the obtained EPS granules, were added.

Example 13 (Comparative Example—DOPS-OH 5.0%+MeITS 10.0%)

Example 1 was repeated with the difference that 5% by weight of 10-hydroxy-9,10-dihydro-9-oxa-10-phosphaphenanthrene-10-thione or -10-sulfide (DOPS-OH) and 10% by weight of melaminium thiosulfate (MeITS), based on the obtained EPS granules, were added.

Example 14 (Comparative Example—DOPO 5.0%+Vultac TB7 10.0%)

Example 1 was repeated with the difference that 5% by weight of 9,10-dihydro-9-oxa-10-phosphaphenanthrene-10-oxide (DOPO) and 10% by weight of para-tertio-butylphenol-disulfide polymer (Vultac TB7), based on the obtained EPS granules, were added.

Example 15 (Exemplary Embodiment—DOPO-ONH$_4$ 3.0%+MeITS 6.5%)

Example 1 was repeated with the difference that 3% by weight of 10-hydroxy-9,10-dihydro-9-oxa-10-phosphaphenanthrene-10-oxide ammonium salt (DOPO-ONH$_4$) and 6.5% by weight of melaminium thiosulfate (MeITS), based on the obtained EPS granules, were added.

Example 16 (Exemplary Embodiment—DOPO-ONH$_4$ 3.0%+Vultac TB7 6.5%)

Example 1 was repeated with the difference that 3% by weight of 10-hydroxy-9,10-dihydro-9-oxa-10-phosphaphenanthrene-10-oxide ammonium salt (DOPO-ONH$_4$) and 6.5% by weight of para-tertiobutylphenol-disulfide polymer (Vultac TB7), based on the obtained EPS granules, were added.

Example 17 (Exemplary Embodiment—DOPO-OH 3.0%+Vultac TB7 6.5%)

Example 1 was repeated with the difference that 3% by weight of 10-hydroxy-9,10-dihydro-9-oxa-10-phosphaphenanthrene-10-oxide (DOPO-OH) and 6,5% by weight of para-tertiobutylphenol-disulfide polymer (Vultac TB7), based on the obtained EPS granules, were added.

Example 18 (Exemplary Embodiment—DOPO-ONH$_4$ 3.0%+ATS 6.5%)

Example 1 was repeated with the difference that 3% by weight of 10-hydroxy-9,10-dihydro-9-oxa-10-phosphaphenanthrene-10-oxide ammonium salt (DOPO-ONH$_4$) and 6.5% by weight of ammonium thiosulfate (ATS—Sigma Aldrich), based on the obtained EPS granules, were added.

Example 19 (Exemplary Embodiment—DOPO-ONH$_4$ 1.0%+MeITS 2.2%)

Example 1 was repeated with the difference that 1% by weight of 10-hydroxy-9,10-dihydro-9-oxa-10-phosphaphenanthrene-10-oxide ammonium salt (DOPO-ONH$_4$) and 2.2% by weight of melaminium thiosulfate (MeITS), based on the obtained EPS granules, were added.

Example 20 (Reference Example—HBCD 2.5%)

Example 1 was repeated with the difference that 2.5% by weight of hexabromocyclododecane (HBCD—FR 1207, ICL-IP company), based on the obtained EPS granules, were dosed.

Example 21 (Exemplary Embodiment—DOPO-ONH$_4$ 5.0%+MeITS 10.0%+Graphite 4.0%)

Example 7 was repeated with the difference that additional 4% by weight of macrocrystalline natural graphite (UF2—Grafit Kropfmühl company), based on the obtained EPS granules, were added.

Example 22 (Exemplary Embodiment—DOPO-ONH$_4$ 3.0%+MeITS 6.5%+Graphite 4.0%)

Example 15 was repeated with the difference that additional 4% by weight of macrocrystalline natural graphite (UF2—Grafit Kropfmühl company), based on the obtained EPS granules, were added.

Example 23 (Reference Example—HBCD 2.5%+Graphite 4.0%)

Example 20 was repeated with the difference that additional 4% by weight of macrocrystalline natural graphite (UF2—Grafit Kropfmühl company), based on the obtained EPS granules, were added.

Example 24 (Exemplary Embodiment PS/CAB—DOPO-ONH$_4$ 5.0%+MeITS 10.0%+Graphite 4.0%)

To a 50/50 mixture of styrene polymer (SUNPOR EPS-STD: 6% by weight of pentane, chain length MW=200,000 g/mol, multiplicity MW/Mn=2.5) and cellulose acetate butyrate (CAB 500-5, Eastman company), 5.0% by weight of 10-hydroxy-9,10-dihydro-9-oxa-10-phosphaphenanthrene-10-oxide ammonium salt (DOPO-ONH$_4$), 10% by weight of melaminium thiosulfate (MeITS) and 4% by weight of macrocrystalline natural graphite (UF2—Grafit Kropfmühl company), based on the obtained polymer mix, were mixed in the inlet of a twin-screw extruder and fused at 190° C. within the extruder. The polymer melt thus obtained was aerated with 3% of a pentane isomeric mixture (80% n-pentane, 20% iso-pentane) and passed through a nozzle plate at a throughput of 20 kg/h and granulated into compact EPS granules using a pressurized underwater granulator.

Example 25 (Comparative Example PS/CAB—HBCD 2.5%+Graphite 4.0%)

To a 50/50 mixture of styrene polymer (SUNPOR EPS-STD: 6% by weight of pentane, chain length MW=200,000 g/mol, multiplicity MW/Mn=2.5) and cellulose acetate butyrate (CAB 500-5, Eastman company), 2.5% by weight of hexabromocyclododecane (HBCD—FR 1207 ICL-IP company) and 4% by weight of macrocrystalline natural graphite (UF2—Grafit Kropfmühl company), based on the obtained polymer mix, were mixed in the inlet of a twin-screw extruder and fused at 190° C. within the extruder. The polymer melt thus obtained was aerated with 3% of a pentane isomeric mixture (80% n-pentane, 20% iso-pentane) and passed through a nozzle plate at a throughput of 20 kg/h and granulated into compact EPS granules using a pressurized underwater granulator.

Table 1 below juxtaposes the results in a lucid manner, with fire behavior of defined test bodies, stability, and time to collapse of the foamed foam beads as well as odor having been evaluated.

TABLE 1

Evaluation of the inventive polymerizates and polymer foams

| | | Fire test | Stability | Odor |
|---|---|---|---|---|
| Example 1 | exemplary embodiment | 3 | 1 | 1 |
| Example 2 | exemplary embodiment | 3 | 1 | 1 |
| Example 3 | exemplary embodiment | 4 | 1 | 1 |
| Example 4 | exemplary embodiment | 4 | 1 | 1 |
| Example 5 | comparative example | 5 | 1 | 1 |
| Example 6 | comparative example | 5 | 1 | 2 |
| Example 7 | exemplary embodiment | 1 | 1 | 1 |
| Example 8 | exemplary embodiment | 2 | 1 | 1 |
| Example 9 | exemplary embodiment | 2 | 1 | 1 |
| Example 10 | exemplary embodiment | 1 | 1 | 2 |
| Example 11 | exemplary embodiment | 1 | 1 | 2 |
| Example 12 | exemplary embodiment | 2 | 1 | 3 |
| Example 13 | comparative example | 3 | 1 | 3 |
| Example 14 | comparative example | 3 | 3 | 2 |
| Example 15 | exemplary embodiment | 2 | 1 | 1 |
| Example 16 | exemplary embodiment | 2 | 1 | 2 |
| Example 17 | exemplary embodiment | 2 | 1 | 2 |
| Example 18 | exemplary embodiment | 3 | 1 | 3 |
| Example 19 | exemplary embodiment | 4 | 1 | 1 |
| Example 20 | reference example | 1 | 1 | 1 |
| Example 21 | exemplary embodiment | 1 | 1 | 1 |
| Example 22 | exemplary embodiment | 2 | 1 | 1 |
| Example 23 | reference example | 1 | 1 | 1 |
| Example 24 | exemplary embodiment | 3 | 1 | 2 |
| Example 25 | exemplary embodiment | 3 | 1 | 2 |

The results in the three right-hand columns were obtained by testing with products of the above described Examples 1 through 25.

In detail:

Fire Test (Column 3 in Table 1):

The EPS granules and/or EPS/CAB granules obtained from the examples were pre-foamed into foam beads with a crude density of 15 to 25 kg/m$^3$ using saturated aqueous vapor, stored for 24 hrs and shaped into foam plates in an automated device for molded components.

Test bodies with a thickness of 2 cm were cut from the foam plates, which were subjected to a fire test according to DIN 4102-2 (B2-small-burner test) after 72 hrs of conditioning at 70° C.

The results rated with numbers between 1 and 5 were evaluated in comparison to EPS rendered flameproof using hexabromocyclododecane (HBCD) (reference examples 20 and 23). Thereby, in the "Fire test" column, a rating of 1 means that the test substance behaves equally well as HBCD-protected EPS regarding its fire behavior. Values of 5 mean that the fire behavior is very poor and equals that of non-fire-retardant EPS.

Stability of Foam Structures (Column 4 in Table 1):

The EPS granules and/or EPS/CAB granules obtained from the examples were exposed to saturated aqueous vapor, and the time until collapse of beads occurred was determined. This time was evaluated in the summary of results in comparison to EPS particles without any flame retardant. Only Example 14 showed a softening effect. All other phosphorus-based flame retardants exhibited equally good stability (no collapse until the end of pre-foaming).

In the "Stability" column, a rating of 1 means that the beads had normal stability. Values of 5 means that the beads collapsed immediately without a foam structure being generated that would be suitable for preparing molded components.

Odor (Column 5 in Table 1):

The EPS granules and/or EPS/CAB granules obtained from the examples were pre-foamed into foam beads with a crude density of 15 to 25 kg/m$^3$ using saturated aqueous vapor, stored for 24 hrs and shaped into foam plates in an automated device for molded components.

Test bodies with a thickness of 2 cm were cut from the foam plates, which were subjected to a sensory odor test by several members of the laboratory staff. Evaluation was subjective according to the criteria "imperceptible", which equals a rating of 1, up to "unpleasantly irritating", equaling a rating of 5.

Evaluation and Discussion of the Results (Table 1):

Examples 1 through 4 show the basic effectiveness of DOPO-OH and its salts DOPO-ONH$_4$, DOPO-OMel and DOPO-Gua as flame retardants.

Examples 5 and 6 show that MeITS and Vultac TB7 alone show no flame-inhibiting effect at equal amounts employed.

Examples 1 and 2 are the reference examples for the effectiveness of sulfur-containing synergists (examples 7 through 12 and 15 through 18), as equal or most of the time even better results regarding flame-inhibiting effects were achieved with equal and lower total concentrations of flame retardant and synergist.

Examples 1 through 4, 7 through 12, 15 through 19 as well as 21 and 22 are examples of expandable polymerizates according to the invention with a flame retardant according to formulae (Ia), (Ib) and/or (Ic).

In examples 1 through 23, EPS was used as a crude material, while in examples 24 and 25 a mixture of polystyrene and cellulose acetate butyrate was used.

Examples 20 and 23 are other references to prior art. All the evalutations in the tests refer to these reference experiments in that the results are marked with numbers from 1 to 5, in which lower numbers, in particular 1, tend to be more favorable while higher numbers, in particular 5, are less favorable.

The mechanical stability of the pre-foamed granules or the foam bodies made thereof was not affected discernibly in any of the examples, with the exception of Example 14 (DOPO).

The molded articles made with Vultac TB7 were established to have a slight phenolic odor. The molded articles made from examples 12 and 18 exhibited a stinging smell. Sulfur compounds (H$_2$S-like odor) could clearly be smelled coming from the molded articles from comparative example 13 (DOPS-OH).

The molded articles from examples 24 and 25 had a typical smell of cellulose acetate butyrate also found in the crude material.

The invention claimed is:

1. Flame-retardant expandable polymerizates containing at least one propellant, characterized in that at least one phosphorus compound is contained as a flame retardant, wherein the at least one phosphorus compound has the following formula:

10-hydroxy-9,10-dihydro-9-oxa-10-phosphaphenanthrene-10-oxide ammonium salt:

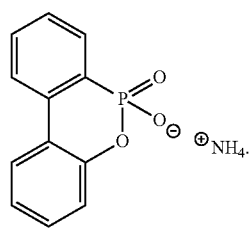

DOPO-ONH$_4$

2. The expandable polymerizates according to claim 1, further comprising 10-hydroxy-9,10-dihydro-9-oxa-10-phosphaphenanthrene-10-oxide guanidinium salt:

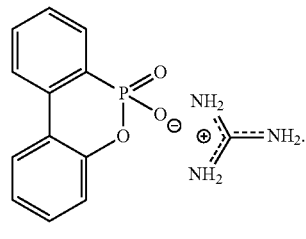

DOPO-OGua

3. The expandable polymerizates according to claim 1, further comprising 10-hydroxy-9,10-dihydro-9-oxa-10-phosphaphenanthrene-10-oxide melaminium salt:

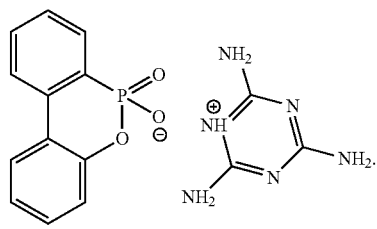

DOPO-OMel

4. The expandable polymerizates according to claim 1, characterized in that the at least one phosphorus compound contained at an amount of 0.5 to 25% by weight based on the total weight of the polymer.

5. The expandable polymerizates according to claim 4, characterized in that the expandable polymerizates are mixtures of styrene polymerizates with expandable thermoplastic polymers, wherein the mixtures of the styrene polymerizates with expandable thermoplastic polymers comprise at least one of: cellulose acetate butyrate (CAB), thermoplastic polyurethane (TPU), and poly(lactic acid), wherein the thermoplastic polymers are contained at 1 to 99% by weight, based on the total polymer weight.

6. The expandable polymerizates according to claim 1, characterized in that, additionally, sulfur and/or at least one sulfur-containing compound and/or sulfur compound is contained as a flame-retardant synergist in the expandable polymerizate.

7. The expandable polymerizates according to claim 6, characterized in that sulfur and/or the at least one sulfur-containing compound and/or sulfur compound are/is contained at an amount of 1 to 25% by weight based on the total weight of the polymer.

8. The expandable polymerizates according to claim 6, characterized in that the expandable polymerizate further comprises a sulfur-containing compound and/or sulfur compound having at least one S—S bond, wherein at least one of said sulfur atoms is present in the bivalent form comprising ammonium thiosulfate.

9. The expandable polymerizates according to claim 6, characterized in that the sulfur-containing compound and/or sulfur compounds exhibit a weight loss of less than 10% by weight in an analysis using thermogravimetry below 115° C.

10. The expandable polymerizates according to claim 6, characterized in that the flame-retardant synergist is melamine thiosulfate and/or bis[(2,4,6-tri-amino-1,3,5-triazinium)thiosulfate:

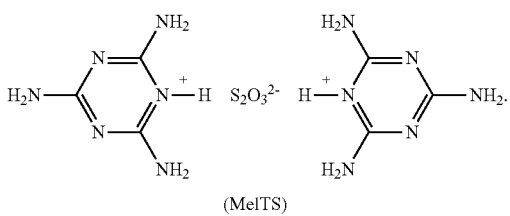

(MelTS)

11. The expandable polymerizates according to claim 6, characterized in that the flame-retardant synergist is para-tertiobutylphenol disulfide polymer:

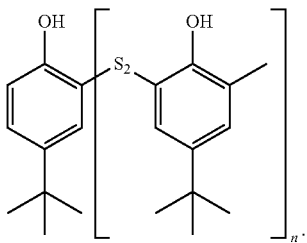

12. A method of preparing flame-retardant, expandable polymerizates according to claim 1, wherein the at least one phosphorus compound is added as a flame retardant to a polymerizate, and the polymerizate is rendered expandable by adding the at least one propellant.

13. The method of preparing flame-retardant expandable polymerizates, according to claim 12, wherein the at least one phosphorus compound, melaminium thiosulfate, and the at least one propellant are mixed with melt of polymerizate, using a dynamic and/or static mixer and then granulated, or wherein the at least one phosphorus compound and melaminium thiosulfate are admixed to granulated polymerizate, using a dynamic and/or static mixer, and fused to form a melt, and the melt is then treated with the at least one propellant and granulated, or wherein the at least one phosphorus compound and melaminium thiosulfate are admixed to granulated polymerizate, using a mixer, and the mixture is then fused and granulated, or wherein the expandable polymerizate is formed into a granulate, and the granulate preparation is by suspension polymerization, in an aqueous suspension in the presence of the at least one phosphorus compound, melaminium thiosulfate and the at least one propellant.

14. The expandable polymerizates according to claim 4, wherein the phosphorus compound(s) is/are contained at an amount of 1 to 15% by weight, based on the total weight of the polymer.

15. The expandable polymerizates according to claim 7, wherein the sulfur and/or the at least one sulfur-containing compound and/or sulfur compound are/is contained at an amount of 2 to 15% by weight based on the total weight of the polymer.

16. The expandable polymerizates according to claim 7, wherein the expandable polymerizates are contained within a pressurized container.

17. The expandable polymerizates according to claim 1, wherein the expandable polymerizates comprise styrene polymerizates (EPS).

* * * * *